United States Patent
Kawazoe

(10) Patent No.: US 8,334,410 B2
(45) Date of Patent: Dec. 18, 2012

(54) METHOD FOR PRODUCING 3-MERCAPTOANILINE COMPOUND

(75) Inventor: Kentaro Kawazoe, Fuji (JP)

(73) Assignee: Ihara Chemical Industry Co., Ltd., Tokyo (JP)

( * ) Notice: Subject to any disclaimer, the term of this patent is extended or adjusted under 35 U.S.C. 154(b) by 184 days.

(21) Appl. No.: 12/743,389

(22) PCT Filed: Nov. 28, 2008

(86) PCT No.: PCT/JP2008/003519
§ 371 (c)(1),
(2), (4) Date: May 18, 2010

(87) PCT Pub. No.: WO2009/069311
PCT Pub. Date: Jun. 4, 2009

(65) Prior Publication Data
US 2010/0249462 A1 Sep. 30, 2010

(30) Foreign Application Priority Data
Nov. 30, 2007 (JP) ................................. 2007-310536

(51) Int. Cl.
C07C 209/00 (2006.01)
C07C 323/00 (2006.01)
C07C 317/00 (2006.01)
(52) U.S. Cl. .................... 564/440; 564/416; 568/30
(58) Field of Classification Search ................ 564/416, 564/440; 568/30
See application file for complete search history.

(56) References Cited

FOREIGN PATENT DOCUMENTS
JP 01-168662 7/1989

OTHER PUBLICATIONS

V. Petrow et al., A New Route to Disulphamyl Derivatives of Benzene, Journal of Pharmacy and Pharmacology, 1960, vol. 12, No. 12, pp. 705-719, Route ii, 5-Chloro-4-nitrotoluene-2-sulphonchloride, p. 716.

W. Palmer Wynne, Studies in the Toluene Series, Part VI, Nitration of the 4-Chloro-toluene-2- and 3-sulphonic Acids, 3-Chlorotoluene-6-sulphonic Acid and their Sulphonyl Chlorides, Journal of the Chemical Society, 1936, pp. 696-707, pp. 698, 706, 707.

Louis A. Carpino, et at., The 2-Chloro-3-indenylmethyloxycarbonyl and Benz[f]inden-3-ylmethyloxycarbonyl Base-Sensitive Amino-Protecting Groups, Application to an Inverse Merrifield Approach to Peptide Synthesis, J. Org. Chem., 1990, 55, pp. 251-259, 3-Nitro-4-methoxybenzenesulfonyl Chloride, p. 256.

Xiao-Hua Du et al., A Novel Synthesis of 2-Chloro-4-Fluoro-5-Nitrobenzenesulfonyl Chloride, Org. Prep. Proced. Int., 2005, vol. 37, No. 6, pp. 566-569, step c, pp. 566,568.

William O. Kermack at al., 3-Nitro- and 3-Amino-4-hydroxybenzenesulphonamicle, Journal of the Chemical Society, 1939, pp. 608-610, Experimental, p. 609.

Primary Examiner — Porfirio Nazario Gonzalez
(74) Attorney, Agent, or Firm — Bacon & Thomas, PLLC

(57) ABSTRACT

A method for producing a 3-mercaptoaniline compound, which is a known intermediate for a 3-(1H-1,2,4-triazol-1-yl) phenylsulfide derivative, useful as a pesticide, and a method for producing a compound which can be used as a starting material in producing the 3-mercaptoaniline compound are disclosed. In one embodiment the nitro group and the chlorosulfonyl group of a 3-nitrobenzenesulfonyl chloride compound represented by general formula (1):

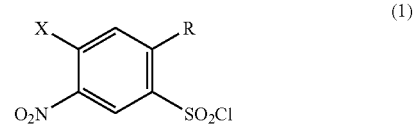

are reduced in the presence of an acid catalyst to produce a compound of general formula (2):

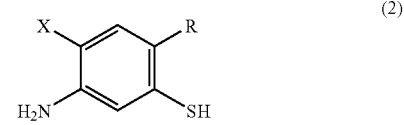

In the above general formulas (1) and (2), R represents an alkyl group or a cyclic alkyl group, and X represents a halogen atom.

10 Claims, No Drawings

METHOD FOR PRODUCING 3-MERCAPTOANILINE COMPOUND

TECHNICAL FIELD

The present invention relates to a method for producing a 3-mercaptoaniline compound and a method for producing a compound to be used as a raw material in the above method.

BACKGROUND ART

There is known, for production of a known compound useful as an insecticide, a miticide and a nematicide, a production method via a 3-mercaptoaniline compound (Patent Literature 1). In the Literature is described, in order to produce a 3-(1H-1,2,4-triazol-1-yl)phenylsulfide derivative, a method of subjecting a 3-mercaptoaniline compound to Salkylation, then conducting diazotization and hydrazine formation, and forming a triazole ring. In the Literature is also described, as a production method of a 3-mercaptoaniline compound, a method of subjecting an acetanilids derivative to chlorosulfonylation and then conducting reduction and hydrolysis. However, the present invention method is not described in the Literature.
Patent Literature 1: Wo 2006/043635

DISCLOSURE OF THE INVENTION

Task to be Achieved by the Invention

The present invention was made in order to provide a method for efficiently and easily producing a 3-mercaptoaniline compound which is known as an intermediate for easy and efficient production of a 3-(1H-1,2,4-triazol-1-yl)phenylsulfide derivative useful as an insecticide, a miticide and a nematicide, and a method for easily producing a compound used as a raw material in the above method.

Means for Achieving the Task

In view of the above situation, the present inventor made a study on the method for producing the 3-mercaptoaniline compound. As a result, it was found unexpectedly that the above task could be achieved by reacting a benzenesulfonyl chloride compound with a nitrating agent at a low temperature to introduce nitro group into the benzenesulfonyl chloride compound while maintaining a high regioselectivity and then reducing the chlorosulfonyl group and nitro group of the obtained 3-nitrobenzenesulfonyl chloride compound preferably in one reactor in one step. The finding has led to the completion of the present invention.

EFFECT OF THE INVENTION

The present invention provides a method for producing a 3-mercaptoaniline compound easily and efficiently. According to the present invention method, an intended 3-mercaptoaniline compound can be produced, with no special reactor required and under mild conditions, at a high selectivity, efficiently, and in an easy operation, by reacting benzenesulfonyl chloride with a nitrating agent at a low temperature to introduce nitro group into the benzenesulfonyl chloride while maintaining a high regioselectivity and then reducing the chlorosulfonyl group and nitro group of the obtained 3-nitrobenzenesulfonyl chloride compound preferably in one reactor in one step.

BEST MODE FOR CARRYING OUT THE INVENTION

The present invention is described in detail below.
The present invention has achieved the above-mentioned task by providing the inventions of the following [1] to [13].
[1] A method for producing a 3-mercaptoaniline compound represented by the general formula (2)

[formula 2]

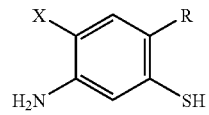

(2)

(wherein R is an alkyl group or a cyclic alkyl group, and X is a halogen atom), characterized by reducing, in the presence of an acid catalyst, the nitro group and chlorosulfonyl group of a 3-nitrobenzenesulfonyl chloride compound represented by the general formula (1)

[formula 1]

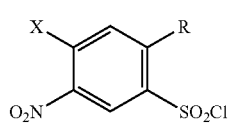

(1)

(wherein R and X have the same definitions as given above).
[2] A method for producing a 3-mercaptoaniline compound according to [1], wherein the reduction is conducted using zinc.
[3] A method for producing a 3-mercaptoaniline compound according to [1] or [2], wherein the acid catalyst is sulfuric acid.
[4] A method for producing a 3-mercaptoaniline compound according to any of [1] to [3], wherein the nitro group and chlorosulfonyl group are reduced in one step.
[5] A method for producing a 3-mercaptoaniline compound according to any of [1] to [3], wherein the nitro group and chlorosulfonyl group are reduced in a plurality of steps.
[6] A method for producing a 3-mercaptoaniline compound according to any of [1] to [5], wherein the reduction is conducted using an alcohol as a solvent.
[7] A method for producing a 3-mercaptoaniline compound according to any of [1] to [6], wherein R is a methyl group and X is a fluorine atom.
[8] A method for producing a 3-nitrobenzenesulfonyl chloride compound represented by the general formula (1)

[formula 4]

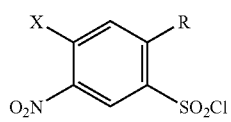

(1)

(wherein R is an alkyl group or a cyclic alkyl group, and X is a halogen atom), characterized by nitrating, in the presence of an acid catalyst, a benzenesulfonyl chloride compound represented by the general formula (3)

[formula 3]

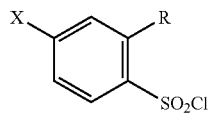

(3)

(wherein R and X have the same definitions as given above).
[9] A method for producing a 3-nitrobenzenesulfonyl chloride compound according to [8], wherein the reaction temperature is 10° C. or lower.
[10] A method for producing a 3-nitrobenzenesulfonyl chloride compound according to [8], wherein the reaction temperature is −30° C. to 10° C.
[11] A method for producing a 3-nitrobenzenesulfonyl chloride compound according to [8], wherein the reaction temperature is −10° C. to 10° C.
[12] A method for producing a 3-nitrobenzenesulfonyl chloride compound according to [8], wherein the reaction temperature is −10° C. to 0° C.
[13] A method for producing a 3-nitrobenzenesulfonyl chloride according to any of [8] to [12], wherein R is a methyl group and X is a fluorine atom.

The present invention is described in detail below.

The present invention provides a method for producing a 3-mercaptoaniline compound represented by the general formula (2) and a method for producing a 3-nitrobenzenesulfonyl chloride compound represented by the general formula (1), to be used as a raw material in the above method.

The 3-mercaptoaniline compound represented by the general formula (2) can be produced by reducing a 3-nitrobenzenesulfonyl chloride compound represented by the general formula (1), which is produced by nitrating a benzenesulfonyl chloride compound (raw material) represented by the general formula (3).

First, description is made on the benzenesulfonyl chloride compound (raw material) represented by the general formula (3), which is used as a raw material for production of the 3-nitrobenzenesulfonyl chloride compound represented by the general formula (1).

In the general formula (3), R is a straight chain or branched chain alkyl group of 1 to 6 carbon atoms (hereinafter, such carbon atoms are abbreviated as "C1 to C6", in this case), such as methyl group, ethyl group, n-propyl group, isopropyl group, n-butyl group, sec-butyl group, tert-butyl group, n-pentyl group, n-hexyl group or the like [the alkyl group may have substituent groups such as straight chain or branched chain C1 to C6 alkyl group (e.g. methyl group, ethyl group, n-propyl group, isopropyl group, n-butyl group, secbutyl group, tert-butyl group, n-pentyl group or n-hexyl group), cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), hydroxy group, straight chain or branched chain C1 to C6 alkoxy group (e.g. methoxy group, ethoxy group, n-propoxy group or isopropoxy group), tri(straight or branched C1 to C6 alkyl)siloxy group (e.g. trimethylsiloxy group or tert-butyldimethylsiloxy group), straight chain or branched chain C1 to 06 hydroxyalkyl group (e.g. hydroxymethyl group or hydroxyethyl group), straight chain or branched chain (C1 to 06 alkoxy)-(C1 to 06 alkyl) group (e.g. methoxymethyl group, methoxyethyl group or ethoxyethyl group), straight chain or branched chain C1 to C6 haloalkyl group (e.g. fluoromethyl group, difluoromethyl group or trifluoromethyl group), nitro group, amino group, mono or di(straight chain or branched chain C1 to 06 alkyl)amino group (e.g. methylamino group, ethylamino group or dimethylamino group), straight chain or branched chain C1 to C6 alkylcarbonylamino group (e.g. methylcarbonylamino group or ethylcarobnylamino group), cyano group, formyl group, straight chain or branched chain C1 to C6 alkylcarbonyl group (e.g. methylcarbonyl group or ethylcarbonyl group), carboxyl group or metal salt thereof, straight chain or branched chain C1 to C6 alkoxycarbonyl group (e.g. methoxycarbonyl group or ethoxycarbonyl group), aminocarbonyl group, mono or di(straight chain or branched chain C1 to C6 alkyl)aminocarbonyl group (e.g. methylaminocarbonyl group, ethylaminocarbonyl group or dimethylaminocarbonyl group), phenyl group, phenoxy group, heteroaryl group (e.g. pyridyl group, thienyl group of furyl group), and the like]; or a cyclic C3 to C6 alkyl group such as cyclopropyl group, cyclobutyl group, cyclopentyl group, cyclohexyl group or the like [the cyclic alkyl group may have substituent groups such as straight chain or branched chain C1 to C6 alkyl group (e.g. methyl group, ethyl group, n-propyl group, isopropyl group, n-butyl group, sec-butyl group, tert-butyl group, n-pentyl group or n-hexyl group), cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), hydroxy group, straight chain or branched chain C1 to C6 alkoxy group (e.g. methoxy group, ethoxy group, n-propoxy group or isopropoxy group), tri (straight or branched C1 to C6 alkyl)siloxy group (e.g. trimethylsiloxy group or tert-butyldimethylsiloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), straight chain or branched chain C1 to C6 haloalkyl group (e.g. fluoromethyl group, difluoromethyl group or trifluoromethyl group), nitro group, amino group, mono or di(straight chain or branched chain C1 to C6 alkyl) amino group (e.g. methylamino group, ethylamino group or dimethylamino group), straight chain or branched chain C1 to C6 alkylcarbonylamino group (e.g. methylcarbonylamino group or ethylcarobnylamino group), cyano group, formyl group, straight chain or branched chain C1 to C6 alkylcarbonyl group (e.g. methylcarbonyl group or ethylcarbonyl group), carboxyl group or metal salt thereof, straight chain or branched chain C1 to C6 alkoxycarbonyl group (e.g. methoxycarbonyl group or ethoxylcarbonyl group), aminocarbonyl group, mono or di(straight chain or branched chain C1 to C6 alkyl)aminocarbonyl group (e.g. methylaminocarbonyl group, ethylaminocarbonyl group or dimethylaminocarbonyl group), phenyl group, phenoxy group, heteroaryl group (e.g. pyridyl group, thienyl group of furyl group), and the like]; and X is a halogen atom such as fluorine atom, chlorine atom, bromine atom, iodine atom or the like.

As specific examples of the benzenesulfonyl chloride compound (raw material compound) represented by the general formula (3), there can be mentioned 4-fluoro-2-methylbenzenesulfonyl chloride, 4-chloro-2-methylbenzenesulfonyl chloride, 4-bromo-2-methylbenzenesulfonyl chloride, 2-ethyl-4-fluorobenzenesulfonyl chloride, 2-chloro-2-ethylbenzenesulfonyl chloride, 4-bromo-2-ethylbenzenesulfonyl chloride, 4-fluoro-2-isopropylbenzenesulfonyl chloride, 4-chloro-2-isopropylbenzenesulfonyl chloride, 4-bromo-2-isopropylbenzenesulfonyl chloride, 2-cyclopropyl-4-fluorobenzenesulfonyl chloride, 4-chloro-2-cyclopropylbenzensulfonyl chloride and 4-bromo-2-cylopropylbenzenesulfonyl chloride. In these compounds, the substituent group corresponding to the general formula R may further have substituents such as straight chain or branched chain C1 to C6 alkyl group (e.g. methyl group, ethyl group, n-propyl group, isopropyl group, n-butyl group, sec-butyl group, tert-butyl group, n-pentyl group or n-hexyl group), cyclic C3 to C6 alkyl group (e.g. cyclopropyl group, cyclobutyl group, cyclopentyl group or cyclohexyl group), tri(straight chain or branched chain C1 to C6 alkyl)silyl group (e.g. trimethylsilyl group or tert-butyldimethylsilyl group), hydroxy group, straight chain or branched chain C1 to C6 alkoxy group (e.g. methoxy group, ethoxy group, n-propoxy group or isopropoxy group), tri(straight or branched C1 to C6 alkyl)siloxy group (e.g. trimethylsiloxy group or tertbutyldimethylsiloxy group), straight chain or branched chain C1 to C6 hydroxyalkyl group (e.g. hydroxymethyl group or hydroxyethyl group), straight chain or branched chain (C1 to C6 alkoxy)-(C1 to C6 alkyl) group (e.g. methoxymethyl group, methoxyethyl group or ethoxyethyl group), straight chain or branched chain C1 to C6 haloalkyl group (e.g. fluoromethyl group, difluoromethyl group or trifluoromethyl group), nitro group, amino group, mono or di (straight chain or branched chain C1 to C6 alkyl)amino group (e.g. methylamino group, ethylamino group or dimethylamino group), straight chain or branched chain C1 to C6 alkylcarbonylamino group (e.g. methylcarbonylamino group or ethylcarobnylamino group), cyano group, formyl group, straight chain or branched chain C1 to C6 alkylcarbonyl group (e.g. methylcarbonyl group or ethylcarbonyl group), carboxyl group or metal salt thereof, straight chain or branched chain C1 to C6 alkoxycarbonyl group (e.g. methoxycarbonyl group or ethoxycarbonyl group), aminocarbonyl group, mono or di (straight chain or branched chain C1 to C6 alkyl)aminocarbonyl group (e.g. methylaminocarbonyl group, ethylaminocarbonyl group or dimethylaminocarbonyl group), phenyl group, phenoxy group, heteroaryl group (e.g. pyridyl group, thienyl group of furyl group), and the like.

Incidentally, the benzenesulfonyl chloride compound (raw material compound) represented by the general formula (3) is a known compound.

Next, description is made on the method for producing a 3-nitrobenzenesulfonyl chloride compound represented by the general formula (1) by nitrating the benzenesulfonyl chloride compound (raw material compound) represented by the general formula (3).

In the nitration reaction, a nitrating agent is used. The nitrating agent used in the reaction may be any nitrating agent which enables the nitration reaction. Specifically, there can be mentioned, for example, fuming nitric acid, concentrated nitric acid, nitric acid, and metal nitrate such as sodium nitrate, potassium nitrate or the like. These nitrating agents may be used singly or in admixture of any mixing ratio. As the nitrating agent usable in the nitration reaction, fuming nitric acid or concentrated nitric acid is preferred from the standpoints of availability, reactivity, etc. and fuming nitric acid is more preferred.

With respect to the use amount of the nitrating agent in the nitration reaction, the reaction proceeds at any molar ratio of the nitrating agent relative to the benzenesulfonyl chloride compound (raw material compound) represented by the general formula (3). However, the nitrating agent is used, for example, in an amount of ordinarily 0.1 to 10.0 mols, preferably 0.33 to 3.0 mols, more preferably 1.0 to 2.0 mols relative to 1 mol of the benzenesulfonyl chloride compound (raw material compound) represented by the general formula (3).

An acid catalyst is used in the nitration reaction. As the acid catalyst, sulfuric acid and phosphoric acid can be mentioned, for example; however, sulfuric acid is preferred. With respect to the use amount of the acid catalyst (represented by sulfuric acid) in the nitration reaction, the reaction proceeds at any molar ratio of the acid catalyst relative to the benzenesulfonyl chloride compound (raw material compound) represented by the general formula (3). However, the acid catalyst is used, for example, in an amount of ordinarily 0.1 to 10.0 mols, preferably 0.33 to 3.0 mols, more preferably 0.5 to 2.0 mols relative to 1 mol of the benzenesulfonyl chloride compound (raw material compound) represented by the general formula (3). The acid catalyst may be used in a large excess when the acid catalyst functions also as a solvent as later described.

The nitration reaction proceeds even in the absence of a solvent; however, a solvent may be used for smooth reaction. The solvent usable in the nitration reaction may be any solvent as long as it does not hinder the reaction. There can be mentioned, for example, sulfuric acid; halogenated hydrocarbons such as dichloroethane, chloroform and the like; aprotic polar solvents such as N,N-dimethylformamide, N,N-dimethylacetamide, acetonitrile, acetone, propylene carbonate and the like; alcohols such as ethanol, isopropanol, ethylene glycol and the like; ethers such as diphenyl ether, tetrahydrofuran and the like; aromatic hydrocarbons such as toluene, xylene and the like; and aliphatic hydrocarbons such as pentane, n-hexane and the like. Use of sulfuric aid as a solvent is preferable because sulfuric acid can function also as the above-mentioned acid catalyst. The above-mentioned solvents can be used singly or in admixture of any mixing ratio. The use amount of the solvent may be such an amount that the reaction system can be stirred sufficiently; however, it is ordinarily 0.05 to 10 liters, preferably 0.3 to 2 liters relative to 1 mol of the benzenesulfonyl chloride compound (raw material compound) represented by the general formula (3).

The temperature of the nitration reaction is, for example, not higher than the reflux temperature of the solvent used. However, it is, for example, 10° C. or lower, preferably −30° C. to 10° C., more preferably −10° C. to 10° C., particularly preferably −10° C. to 0° C., from the standpoint of suppression of formation of regioisomer with respect to nitro group. Since the nitration reaction is an exothermic reaction, it is preferred to conduct the reaction while controlling the reaction temperature by employing a means such as dropping or the like.

With respect to the time of the nitration reaction, there is no particular restriction. However, the reaction time is preferably 1 to 30 hours form the standpoints of by-product suppression, etc.

By conducting the nitration reaction as above, an intended 3-nitrobenzenesulfonyl chloride compound represented by the general formula (1) can be produced easily and at a high regioselectivity of nitro group.

Next, description is made on the method for producing a 3-mercaptoaniline compound represented by the general formula (2) by reducing, in one step or in a plurality of steps, the nitro group and chlorosulfonyl group of the 3-nitrobenzenesulfonyl chloride compound represented by the general formula (1). In the present method, the nitro group and the chlorosulfonyl group can be reduced in one step in one reaction system, and this is a technical feature of the present method.

In the reduction reaction, zinc is used as a reducing agent. With respect to the molar ratio of the reducing agent used in the reduction reaction, the reaction proceeds at any molar ratio relative to the 3-nitrobenzenesulfonyl chloride compound represented by the general formula (1); however, the reducing agent is used, for example, in an amount of ordinarily 1.0 to 20.0 mols, preferably 3.0 to 15.0 mols, more preferably 6.0 to 12.0 mols relative to 1 mol of to the 3-nitrobenzenesulfonyl chloride compound represented by the general formula (1).

An acid catalyst is used in the reduction reaction. The acid catalyst used in the reaction may be any acid catalyst as long as it has an acidity which allows for the progress of the reduction reaction. However, as specific examples, there can be mentioned mineral acids such as hydrochloric acid, sulfuric acid, nitric acid and the like; organic acids such as acetic acid, phosphoric acid and the like; Lewis acids such as aluminum chloride, boron trifluoride tetrahydrofuran complex and the like; and solid acids. Use of mineral acids such as hydrochloric acid, sulfuric acid, nitric acid or the like is preferred from the standpoints of availability, reactivity, etc., and use of hydrochloric acid is more preferred. These acid catalysts may be used singly or in admixture of any mixing ratio.

With respect to the molar ratio of the acid catalyst used in the reduction reaction, the reaction proceeds at any molar ratio relative to the 3-nitrobenzenesulfonyl chloride compound represented by the general formula (1). However, the acid catalyst is used, for example, in an amount of ordinarily 1.0 to 40.0 mols, preferably 3.0 to 30.0 mols, more preferably 6.0 to 24.0 mols relative to 1 mol of the 3-nitrobenzenesulfonyl chloride compound represented by the general formula (1).

The reduction reaction proceeds even in the absence of a solvent. However, a solvent is preferably used for smooth reaction. The solvent usable in the reduction reaction may be any solvent as long as it does not hinder the reaction, and there can be mentioned, for example, alcohols such as methanol, ethanol, isopropanol, ethylene glycol and the like; aprotic polar solvents such as N,N-dimethylformamide, N,N-dimethylacetamide, acetonitrile, acetone, propylene carbonate and the like; ethers such as diphenyl ether, tetrahydrofuran and the like; aromatic hydrocarbons such as toluene, xylene and the like; and aliphatic hydrocarbons such as pentane, n-hexane and the like. Preferred are alcohols such as methanol, ethanol, isopropanol, ethylene glycol and the like and particularly preferred is ethanol. These solvents may be used singly or in admixture of any mixing ratio. The use amount of the solvent may be any amount as long as sufficient mixing of the reaction system is ensured; however, it is ordinarily 0.05 to 10 liters, preferably 0.3 to 2 liters relative to 1 mol of the 3-nitrobenzenesulfonyl chloride compound represented by the general formula (1).

The temperature of the reduction reaction is, for example, 0° C. to the reflux temperature of the solvent used but is preferably 10 to 100° C.

The time of the reduction reaction has no particular restriction but is preferably 1 to 100 hours from the standpoints of suppression of by-product formation, etc.

As explained above, the method of the present invention enables easy production of a 3-mercaptoaniline compound represented by the general formula (2) under mild conditions, at a high selectivity and at a high yield, using no special reactor. The obtained 3-mercaptoaniline compound represented by the general formula (2) is useful as an intermediate for medicine and agricultural chemical.

EXAMPLES

Next, the method for producing the present invention compound is described specifically by way of Examples. However, the present invention is in no way restricted by these Examples.

Example 1

Production of 4-fluoro-6-methyl-3-nitrobenzenesulfonyl Chloride 19.6 g (300 mmol) of fuming nitric acid (d=1.52) and 49 g (500 mmol) of sulfuric acid were placed in a 100-ml four-necked flask equipped with a mechanical stirrer, a thermometer and a dropping funnel. The mixture was cooled to −5 to 0° C. using a freezing mixture with stirring. To the resulting system was dropped 52.2 g (250 mmol) of 4-fluoro-2-methylbenzenesulfonyl chloride while keeping −5 to 0° C., followed by stirring for 3 hours in that temperature range. To the reaction system was slowly added 24.5 g (250 mmol) of sulfuric acid, followed by stirring at 5 to 0° C. for 2 hours and then at room temperature for 2 hours. The reaction mixture was poured onto ice, followed by extraction with ethyl acetate twice. The ethyl acetate layer was washed two times with water and once with a saturated aqueous sodium chloride solution. The ethyl acetate layer was dried with anhydrous sodium sulfate and then subjected to distillation under reduced pressure to remove ethyl acetate to obtain 65.6 g of a yellow oil. The components in the oil were 4-fluoro-6-methyl-3-nitrobenzenesulfonyl chloride (90.0%) and 4-fluoro-6-methyl-5-nitrobenzenesulfonyl chloride (isomer) (9.9%) in an areal ratio based on gas chromatography.

$^1$H NMR (300 MHz, CDCl$_3$) δ:
8.84 (d, J=7.2 Hz, 1H), 7.41 (d, J=11.7 Hz, 1H),
2.90 (s, 3H) ppm
GC-MS: M$^+$=253, (M+2)$^+$=255

Example 2

Production of 4-fluoro-6-methyl-3-nitrobenzenesulfonyl Chloride)

0.1 g (1.5 mmol) of fuming nitric acid (d=1.52), 0.1 g (1 mmol) of sulfuric acid and 0.2 g (1 mmol) of 4-fluoro-2-methylbenzenesulfonyl chloride were placed in a 15-ml test tube type flask equipped with a magnetic stirrer. They were stirred at 20 to 30° C. for 3 hours in a water bath. The components of the reaction mixture were 4-fluoro-6-methyl-3-nitrobenzenesulfonyl chloride (72.7%), 4-fluoro-6-methyl-5-nitrobenzenesulfonyl chloride (isomer) (10.2%) and 4-fluoro-2-methylbenzenesulfonyl chloride (raw material) (14.4%) in an areal ratio based on gas chromatography.

Example 3

Production of 6-fluoro-4-methyl-3-mercaptoaniline 156.9 g (2.4 mol) of zinc, 500 ml of ethanol and then 77 g (0.3 mol) of 4-fluoro-6-methyl-3-nitrobenzenesulfonyl chloride were placed in a 2-liter eggplant-shaped flask equipped with a mechanical stirrer, a thermometer and a dropping funnel. Thereinto was dropped 500 g (5 mol) of hydrochloric acid in a water bath so that the temperature of the reaction system did not exceed 50° C., followed by stirring at 75° C. for 6 hours. Ethanol was distilled off under reduced pressure; the residue was cooled to room temperature; sodium bicarbonate was added to neutralize the reaction system; extraction was conducted twice with ethyl acetate; the ethyl acetate layer was washed with water and then with a saturated aqueous sodium chloride solution. The ethyl acetate layer was dried with anhydrous sodium sulfate and subjected to distillation under reduced pressure to distil off ethyl acetate to obtain 41 g of a title compound at a yield of 87%.

$^1$H NMR (300 MHz, CDCl$_3$) σ:
6.81 (d, J=10.8 Hz, 1H), 6.75 (d, J=8.7 Hz, 1H),
3.14 (s, 1H), 2.22 (s, 3H) ppm
GC-MS: M$^+$=157

The invention claimed is:

1. A method for producing a 3-mercaptoaniline compound represented by the following general formula (2):

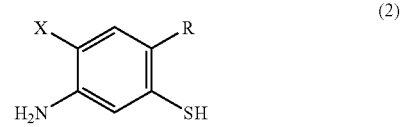

(wherein R is a methyl group, and X is a fluorine atom), the method comprising:

reducing, in the presence of an acid catalyst, the nitro group and chlorosulfonyl group of a 3-nitrobenzenesulfonyl chloride compound represented by the following general formula (1):

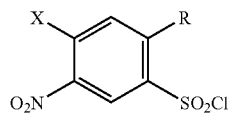
(1)

(wherein R is a methyl group and X is a fluorine atom.

2. A method for producing a 3-mercaptoaniline compound according to claim 1, wherein the reduction is conducted using zinc.

3. A method for producing a 3-mercaptoaniline compound according to claim 1, wherein the acid catalyst is sulfuric acid.

4. A method for producing a 3-mercaptoaniline compound according to claim 1, wherein the nitro group and chlorosulfonyl group are reduced in one step.

5. A method for producing a 3-mercaptoaniline compound according to claim 1, wherein the nitro group and chlorosulfonyl group are reduced in a plurality of steps.

6. A method for producing a 3-nitrobenzenesulfonyl chloride compound represented by the following general formula (1):

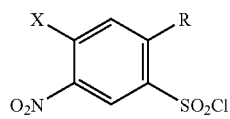
(1)

(wherein R is a methyl group, and X is a fluorine atom), the method comprising:
nitrating, in the presence of an acid catalyst, a benzenesulfonyl chloride compound represented by the following general formula (3):

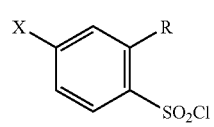
(3)

(wherein R is a methyl group and X is a fluorine atom).

7. A method for producing a 3-mercaptoaniline compound represented by the following general formula (2):

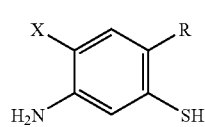
(2)

(wherein R is an alkyl group or a cyclic alkyl group, and X is a halogen atom), the method comprising:
reducing, in the presence of an acid catalyst, the nitro group and chlorosulfonyl group of a 3-nitrobenzenesulfonyl chloride compound represented by the following general formula (1):

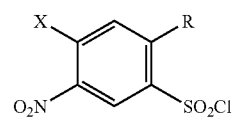
(1)

wherein:
R is an alkyl group or a cyclic alkyl group, and X is a halogen atom; and
the nitro group and the chlorosulfonyl group are reduced in a plurality of steps.

8. A method for producing a 3-mercaptoaniline compound according to claim 7, wherein the reduction is conducted using zinc.

9. A method for producing a 3-mercaptoaniline compound according to claim 7, wherein the acid catalyst is sulfuric acid.

10. A method for producing a 3-nitrobenzenesulfonyl chloride compound represented by the following general formula (1):

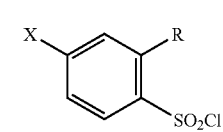
(1)

(wherein R is an alkyl group or a cyclic alkyl group, and X is a halogen atom), the method comprising:
nitrating, in the presence of an acid catalyst and at a temperature of 10° C. or lower, a benzenesulfonyl chloride compound represented by the following general formula (3):

(3)

(wherein R is an alkyl group or a cyclic alkyl group and X is a halogen atom).

* * * * *